US00PP36072P2

(12) United States Plant Patent
Gasic

(10) Patent No.: US PP36,072 P2
(45) Date of Patent: Aug. 20, 2024

(54) PEACH TREE NAMED 'CaroRes Wonder'

(50) Latin Name: *Prunus persica*
Varietal Denomination: CaroRes Wonder

(71) Applicant: CLEMSON UNIVERSITY RESEARCH FOUNDATION, Clemson, SC (US)

(72) Inventor: Ksenija Gasic, Clemson, SC (US)

(73) Assignee: CLEMSON UNIVERSITY RESEARCH FOUNDATION, Clemson, SC (US)

( * ) Notice: Subject to any disclaimer, the term of this patent is extended or adjusted under 35 U.S.C. 154(b) by 0 days.

(21) Appl. No.: 18/445,318

(22) Filed: Jul. 10, 2023

(51) Int. Cl.
*A01H 5/08* (2018.01)
*A01H 6/74* (2018.01)

(52) U.S. Cl.
USPC ..... Plt./197

(58) Field of Classification Search
USPC ..... Plt./156, 194, 197
See application file for complete search history.

*Primary Examiner* — Susan McCormick Ewoldt
*Assistant Examiner* — Zachariah Allan Kay
(74) *Attorney, Agent, or Firm* — Fredrikson & Byron, P.A.

(57) ABSTRACT

A new and distinct peach (*Prunus persica*) cultivar denominated 'CaroRes Wonder' can be distinguished by its melting yellow flesh, early ripening season, large size, attractive appearance, high red skin color, excellent fruit quality, good flavor, fruitlet tolerance to late spring frost, and resistance to bacterial spot disease.

3 Drawing Sheets

Latin name of the genus and species of the plant: *Prunus persica.*

Variety denomination: 'CaroRes Wonder'.

BACKGROUND

A new and distinct peach cultivar named 'CaroRes Wonder' is described herein. The new cultivar originated from a cross between seed parent 'Carored' (not patented) and pollen parent 'Blazeprince' (not patented) in 2009 near Seneca, SC. This new cultivar was selected in 2013 for its potential as a fresh-market peach in South Carolina and the southeast United States. The presently disclosed variety exhibited the outstanding desirable fruit characteristics described below.

Seneca, SC is under a humid subtropical climate. Winters are short and mild with little to no snow; summers are long, hot and humid. There is significant annual rainfall averaging 1339 mm (52.7 in) coming from an average of 116 rainy days a year. July has the greatest amount of rainy days (13.8 days), mostly from thunderstorms, with an average of 88.9 mm (3.5 in) rainfall, and rarely exceeding 175 mm (6.9 in) or falling below 33 mm (1.3 in). The average high temperature in the warmest month, also July, is 32° C., with an average heat index at 40° C. The average low temperature in the coldest month, January, is 0.8° C. The hours below 7° C. varies greatly year to year, but range between 700-1200 hours.

The original plant selection was propagated asexually by budding onto standard peach rootstock cultivar Guardian® (not patented) and a test plot of two plants was established in Seneca, SC. Subsequently, larger test plantings were established with asexually multiplied plants at two additional locations in South Carolina (near Ridge Springs, SC). At each location, propagation was by budding onto the standard peach rootstock cultivar Guardian® (not patented)

from buds collected at the Seneca test plot. No incompatibility or change of scion attributes with Guardian® (not patented) peach rootstocks have occurred following budding. During all asexual multiplication, the characteristics of the original plant have been maintained and no aberrant phenotypes have appeared. The asexual multiplication demonstrates that such reproduction of the characteristics of the tree are consistent and are established or transmitted through succeeding generations.

BRIEF SUMMARY

The new and distinct peach cultivar originated from a cross between seed parent 'Carored' (not patented) and pollen parent 'Blazeprince' (not patented) made in 2009 near Seneca, SC. The seeds resulting from this controlled hybridization were germinated in a greenhouse in the late winter 2009/early spring of 2010 and planted in a test field in Seneca. The seedlings fruited during the summer of 2012 and 2013 and one peach seedling, designated SC09-09-054, was selected for its juicy melting flesh, early season ripening, size consistency, attractive appearance, high red skin color, excellent classic peach flavor, and tolerance to late spring frost and bacterial spot disease. The new cultivar, designated originally as SC09-09-054, tested as SC2, was subsequently named 'CaroRes Wonder'.

The claimed variety is similar to the seed parent 'Carored' (not patented) in that it is early ripening, around May 24$^{th}$ in Seneca. 'CaroRes Wonder' differs from the seed parent 'Carored' by having superior fruit weight and diameter (180 g and 68 mm, compared to 144 g and 65.7 mm). 'CaroRes Wonder' has similar fruit size and weight to the pollen parent 'Blazeprince' (not patented), but ripens about one month earlier than 'Blazeprince', which ripens around June 27$^{th}$ in Seneca. 'CaroRes Wonder' differs from both 'Carored' and 'Blazeprince' by having higher tolerance to low temperatures in the spring and bacterial spot [*Xanthomonas campestris* pv. *pruni* (Smith) Dye] in fruit.

BRIEF DESCRIPTION OF THE DRAWINGS

The accompanying photographs show typical specimens of the new cultivar in color as nearly true as it is reasonably possible to make in a color illustration of this character.

DETAILED BOTANICAL DESCRIPTION

Figure 1:
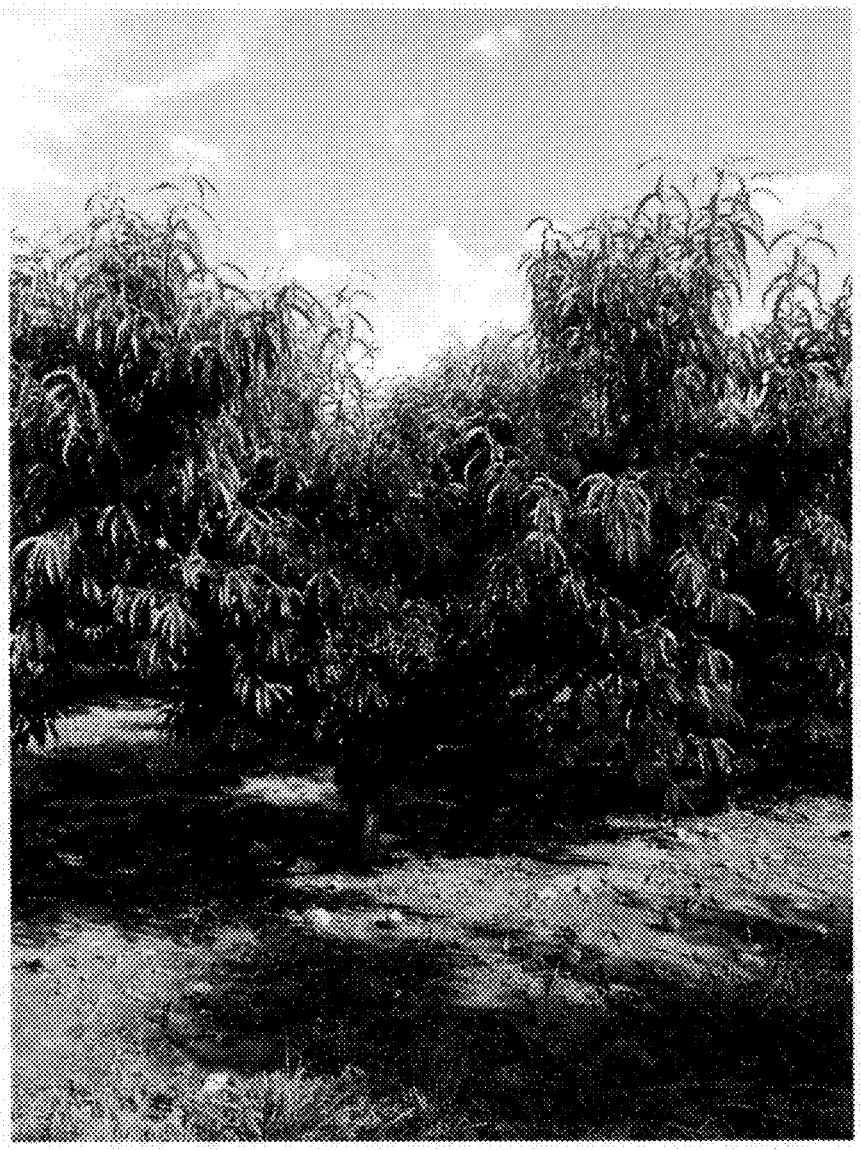
FIG. 1 is a photograph of a tree with mature fruit of 'CaroRes Wonder' at ten years of age.
Figure 2:
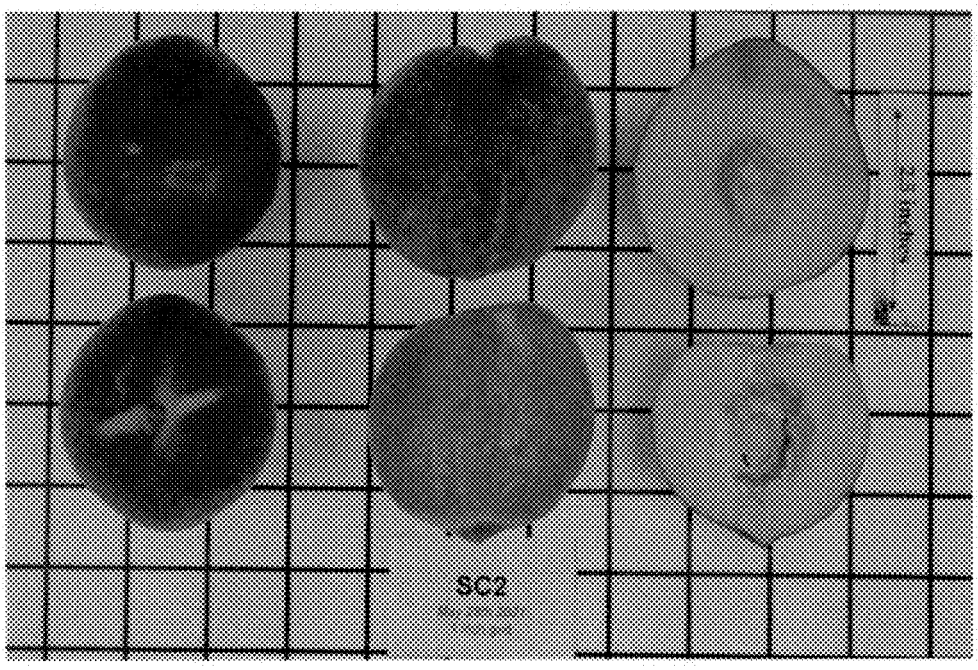
FIG. 2 is a photograph of a whole and longitudinally cut fruit of 'CaroRes Wonder' at maturity at ten years of age.
Figure 3:
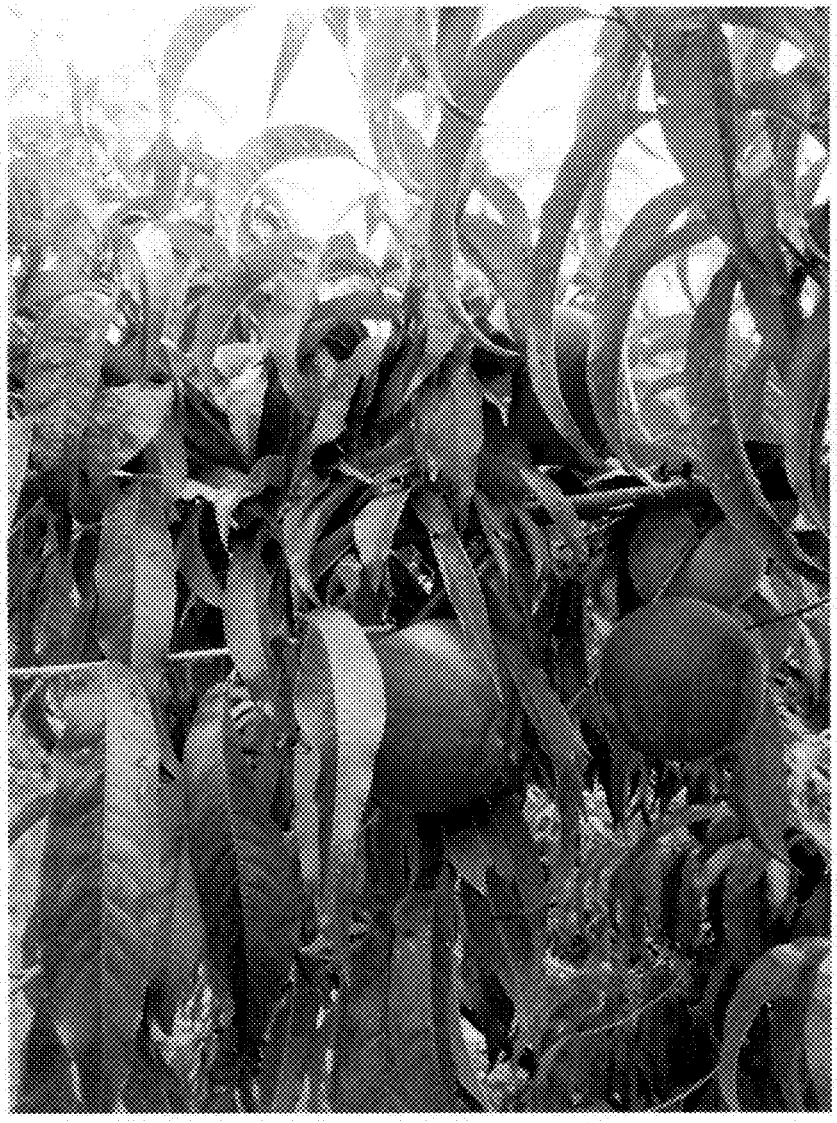
FIG. 3 is a photograph of fruit on the tree of 'CaroRes Wonder' at ten years of age.

Plants and fruit of this new cultivar differ phenotypically from its parents. While 'CaroRes Wonder' has yellow fleshed, melting flesh, textured like its parents ('Carored', the seed parent, and 'Blazeprince', the pollen parent), the fruit of 'CaroRes Wonder' has a superior size than the fruit of 'Carored'. 'CaroRes Wonder' ripens one month and a half earlier than the pollen parent, 'Blazeprince'. Further, 'CaroRes Wonder' has a high tolerance to fruit infection from bacterial spot, where 'Blazeprince' is highly susceptible, and where 'Carored' is moderately susceiptible.

Trees of the new cultivar are vigorous, productive, standard in size, well-branched and symmetrical with an upright to semi-spreading growth habit, comparable to other peach and nectarine trees. Trees express a high level of tolerance to both foliar and fruit infection of bacterial spot [*Xanthomonas campestris* pv. *pruni* (Smith) Dye]. The new cultivar blooms in the spring around end of February to beginning of March, which is on the early range of all cultivars blooming at the test station in Seneca, SC. No winter cold injury has been observed on wood or buds of the new cultivar in South Carolina tests where minimum temperatures have reached 5° F. (−15° C.) during evaluation. Bud chill hardiness ranges from −10 to −15° C. Chilling requirement to break dormancy is estimated to be 35-40 chill portions or 564 hours below 45° F. (7° C.). High tolerance of young fruit to late spring frost down to −5° C.

Fruit of the new cultivar ripens early season, averaging 1 to 5 days before or with 'Carored'. Average first ripening date is May 24th in upstate South Carolina (Seneca). Very few split pits, with uniform shape, but with some fruit with lopsided halves. Fruit yields have been good with an estimated 55.73 kg total yield on $4^{th}$ leaf, open center trees.

The fruit is round in shape with slight tips. Fruits are attractive with greater than 80% red blush. The fruit skin has light pubescence. The flesh of the fruit is yellow in base color with red pigments and flecking. Flesh is of the melting type, but fruit holds well on tree. The fruit is a clingstone, in that the flesh adheres to the pit. Fruit size is large, averaging 175 g. The fresh fruit has excellent classic peach flavor and was rated highly in evaluations. Fruits average 9.8% soluble solids, which is good for the season. Flavor is sweet and well balanced with moderate acidity. The acidity level of 'CaroRes Wonder' is 0.87% malic acid.

The following is a detailed description of the botanical and pomological characteristics of the subject peach. Color data are presented in Royal Horticultural Society Colour Chart designations (2015 $6^{th}$ revised edition). Where dimensions, sizes, colors and other characteristics are given, it is to be understood that such characteristics are approximations of averages set forth as accurately as practical.

Plants used for botanical data were at their $4^{th}$ leaf and grown on berms on a fine sandy loam soil with stake irrigation near Clemson, SC. Trees were trained to an open-center training system and dormant pruned annually. Fruits on all trees were thinned to approximately 6 inches between fruits 4-5 weeks after full bloom. The trees were fertilized near budbreak (late March on average) with 19-19-19 fertilizer. Weeds were controlled with pre- and postemergence herbicides. Routine commercial fungicide and insecticide applications were made to the trees. The descriptions reported herein are from specimens grown near Clemson, SC.

Plant:

*Size*.—Mature trees ($4^{th}$ leaf) average 3.29 m in height and 4.69 m in spread or width, and a semi-upright growth habit, as grown on Guardian® (not patented) rootstock using an open-center training system commonly used on peaches.

*Growth*.—Vigorous, symmetrical form, good canopy development.

*Productivity*.—Good productivity and consistent from year to year. High bud density, and fruit set. Yields averaged 48.08 kg/tree for 'CaroRes Wonder' similar to 'Carored'(not patented) at 62.34 kg/tree.

*Cold hardiness*.—Wood and dormant buds hardy to 5° F. (−15° C.). This was the coldest temperature that the trees were exposed to at the test site, but hardiness may exceed this temperature.

*Disease resistance*.—Leaves and fruit tolerant but not immune to bacterial spot under growing conditions where bacterial spot infection is often very severe on susceptible genotypes. A commercial fungicide program was utilized in orchards used in the development and evaluation of the instant cultivar, thus no resistance to brown rot (*Monilinia fructicola* (G. Winter) Honey) or scab (*Fusicladium carpophilum* (Thum.) Oudem), the other common diseases at Seneca, SC, were determined.

*Insect resistance*.—Insecticides were applied to orchards used in the development of the instant cultivar to control the common insects at the location including oriental fruit moth (*Grapholita molesta* (Busck)), plum curculio (*Conotrachelus nenuphar* (Herbst)), stinkbug (*Halyomorpha halys* (Stal); *Euschistus servus* (Say); *Acrosternum hilare* (Say); *Nezara viridula* (Linnaeus); *Thyanta* spp.), tarnished plant bug (*Lygus lineolaris* (Palisot de Beauvois)), lesser peach tree borer (Synathedon pictipes (Grote & Robinson)), and greater peach tree borer (*Synanthedon exitiosa* (Say)). Therefore, no insect resistance was determined in the testing of the instant cultivar.

Foliage/shoots/branches:

*Shoots*.—Smooth. Dormant-season shoot; Dormant-season shoot color top: Dark Red (N187A); bottom: Green Group 143C.

*Branch*.—Length 51 cm; diameter at base 0.52 cm; diameter at midpoint 0.4 cm; diameter at terminal 0.22 cm.

*Leaves*.—Simple, alternate, glabrous (on both abaxial and adaxial), lanceolate, petiolate, and deciduous. Venation pinnate; base acute; terminal or apex acuminate; margin serrated. Mature leaf size: length 16.6 cm; width midpoint 3.3 cm. Leaf serrations 6 per cm. Mature leaf color: abaxial — Moderate Yellow Green (146B); adaxial — Grayish Olive Green (NN137A). Young leaf color: abaxial — Moderate Yellow Green (146B); adaxial — Strong Yellow Green (144A); Petiole length — mature leaf: 1.1 cm, petiole width: 1.2 mm; petiole texture: smooth no pubescence; petiole strength: strong. Leaf glands: reniform, average of 3.2 per leaf, located at base of leaf blade at top of petiole. Leaf glands are 0.15 cm in length and 0.25 mm in diameter. Stipule length: 7 mm, width: 0.5 mm.

*Buds*.—Number of leaf buds per 15 cm: 14.8, evenly distributed along the shoot. Number of flower buds per 15 cm from terminal: 22.8. Mature shoot internode length: base 2.6 cm, midpoint 2.3 cm, terminal 1.3 cm. Mature shoot internode diameter: base 0.5 cm, midpoint 0.3 cm, apex 0.2 cm.

Bark (of mature trunk of tree):

*Color*.—Dark Greyish Yellowish Brown (N199B).

*Texture*.—Rough.

Trunk:

*Diameter*.—21.84 cm (at 25 cm above ground level).

Flower buds: Dormant flower bud length 0.5 cm and diameter 0.25 cm and color Red Purple Group (59A); dormant buds swell and expand in late winter and increase in size during this expansion to fully open flowers.

Flowers: Bloom occurs prior to vegetative bud break; solitary to occasional double individual flowers at a single node; perfect; self-fertile.

*Date of bloom*.—50%, Julian 62 (March 3); 90%, Julian 66 (March 7) which is early bloom period for all cultivars at the test station in Seneca, SC.

*Size*.—Diameter fully open 2.2 cm. Type — Non-showy.

*Color*.—Adaxial/abaxial: Strong Purplish Pink-55B/Strong Purplish Pink-55B.

*Petals per flower*.—5; length 13.8 mm; width 7.4 mm; texture smooth; shape — teardrop.

*Length of pistil*.—1.7 cm; positioned below anthers in full bloom.

*Width of pistil*.—1 mm.

*Stamens*.—Average 52.2/flower with pollen present, fertile and abundant.

*Ovary*.—Pubescence, round to oval. Light-Yellow Green — 138D.

Fruit:

*Size*.—Large, avg. 175 g; diameter 68 mm. Diameter stem end 6.7 cm, equator 7.3 cm, blossom end 6.6 cm; length base to apex 7.4 cm.

*Shape*.—Round, sometimes assymmetrical with slight tip.

*Skin*.—Light pubescence, attractive; ground color Brilliant Orange Yellow 21B with red blush (Strong Red 46A) covering over 80% of surface on average.

*Flesh*.—Color Light Yellow 160B; clingstone; uniform ripening, melting texture. Firmness 3.63 kg/cm$^2$. Classic peach flavor, sweet, and moderate acid.

*Pedicel length*.—0.9 cm.

*Pedicel diameter*.—0.42 cm.

*Pedicel color*.—Strong Greenish-Yellow 151A.

*Pedicel strength*.—Strong; holds on well.

*Ripe date*.—May 27th (Julian 147) in upstate South Carolina; 'Carored' (not patented) ripens May 28th (Julian 148). Ripening of individual fruit is uniform, sometimes tips can soften first.

*Tendency of pit to split*.—Light splitting. Less splitting than 'Rubyprince' (not patented), similar to 'Carored'(not patented).

*Soluble solids*.—9.8%.

*Fruit juice pH*.—3.6.

*Fruit juice titratable acidity*.—0.74% malic acid.

*Fruit glossiness*.—Weak.

*Storage performance*.—Overall for 0-2 weeks of storage for 'CaroRes Wonder' peforms well and shows no loss in fruit quality.

Pit/stone:

*Size*.—Length 3.8 cm; diameter (midpoint) 2.6 cm.

*Shape*.—Oblong, truncate base, unequal side, furrowing and pitting.

*Color*.—Red-Purple (59C) when flesh freshly cut.

Kernel:

*Size*.—Length 1.8 cm; diameter 1.02 cm.

*Shape*.—Ovate with acute tip and obtuse base.

*Color*.—Brownish Orange (165B) when fresh.

Uses: Fresh consumption, not evaluated for drying or other uses.

The cultivar: The outstanding characteristics of 'CaroRes Wonder' are attractive appearance, yellow fleshed peach, firm but melting texture, and bacterial spot tolerance. It stands out from other cultivars due to size consistency, excellent eating quality, and tolerance to low spring temperatures and disease.

The invention claimed is:

1. A new and distinct cultivar of peach tree named 'CaroRes Wonder,' substantially as illustrated and described herein.

* * * * *